(12) United States Patent
Martin et al.

(10) Patent No.: US 9,505,790 B2
(45) Date of Patent: Nov. 29, 2016

(54) SILANE COMPOUNDS AND THEIR USE IN FUNCTIONALIZING SOLID SUPPORTS AND IMMOBILIZING BIOLOGICAL MOLECULES ON THESE SUPPORTS

(75) Inventors: Franck Martin, Montpellier (FR); Michel Granier, Teyran (FR); Gérard Lanneau, Teyran (FR)

(73) Assignees: Commissariat A L'Energie Atomique, Paris (FR); Universite Montpellier II, Montpellier (FR); Centre National De La Recherche Scientifique, Paris (FR)

( * ) Notice: Subject to any disclaimer, the term of this patent is extended or adjusted under 35 U.S.C. 154(b) by 1607 days.

(21) Appl. No.: 12/162,799

(22) PCT Filed: Feb. 1, 2007

(86) PCT No.: PCT/EP2007/050983
§ 371 (c)(1),
(2), (4) Date: Aug. 12, 2008

(87) PCT Pub. No.: WO2007/088186
PCT Pub. Date: Aug. 9, 2007

(65) Prior Publication Data
US 2009/0005269 A1 Jan. 1, 2009

(30) Foreign Application Priority Data
Feb. 1, 2006 (FR) ...................................... 06 50360

(51) Int. Cl.
C07F 7/08 (2006.01)
C07F 7/12 (2006.01)
C07F 7/18 (2006.01)

(52) U.S. Cl.
CPC ............. *C07F 7/0896* (2013.01); *C07F 7/12* (2013.01); *C07F 7/1836* (2013.01); *C07B 2200/11* (2013.01)

(58) Field of Classification Search
None
See application file for complete search history.

(56) References Cited

U.S. PATENT DOCUMENTS 3,794,673 A * 2/1974 Boersma et al. .... C07D 309/12
521/112
4,997,965 A * 3/1991 Lohmann et al. ............ 556/419

FOREIGN PATENT DOCUMENTS

| EP | 1 463 140 | 9/2004 |
|----|-----------|--------|
| PL | 119230 | 12/1981 |
| SU | 846546 | * 7/1979 |
| WO | WO 02/051856 | 7/2002 |

OTHER PUBLICATIONS

Gershevitz et al (2003 JACS 125:4730-4731).*
Leray et al (2000 J. Photochemistry and Photobiology A: Chemistry 132:43-52).*
Lettan II et al (2005 Organic Letters 7:3227-30).*
Schneider et al (1990 Synthesis 11, 1027-31).*
International Search Report completed Apr. 4, 2007, in International Application No. PCT/EP2007/050983, filed Feb. 1, 2007.
French Search Report completed Sep. 7, 2006, in corresponding French Application No. 0650360, filed Feb. 1, 2006.
Gershevitz, Olga, et al., "Molecular monolayer-mediated control over semiconductor surfaces: evidence for molecular depolarization of silane monolayers on $Si/SiO_x$,", J. Am. Chem. Soc., 2003, p. 4730-4731, vol. 125, No. 16.
Pirkle, William, H., et al., "Useful and easily prepared chiral stationary phases for the direct chromatographic separation of the enantiomers of a variety of derivatized amines, amino acids, alcohols and related compounds", J. Org. Chem., 1986, p. 4991-5000, vol. 51, No. 25.
Tillman, Nolan et al., "A novel self-assembled monolayer film containing a sulfone-subsituted aromatic group", Langmuir, 1990, p. 1512-1518, vol. 6, No. 9.
Tillman, Nolan, et al., "Incorporation of phenoxy groups in self-assembled monolayers of trichlorosilane derivatives: effects on film thickness, wettability, and molecular orientation", J. Am. Chem. Soc., 1988, p. 6136-6144, vol. 110, No. 18.

* cited by examiner

*Primary Examiner* — Christopher M Gross
(74) *Attorney, Agent, or Firm* — Brinks Gilson & Lione

(57) ABSTRACT

The invention relates to novel silane compounds corresponding to the following formula (I):

A-E-X     (I)

in which:
X represents a silylated group which makes possible the covalent attachment of the silane compound to the hydroxyl or hydride functional groups of a support;
E represents an organic spacer group;
A represents a group capable of releasing an —OH functional group by acid hydrolysis, the said —OH functional group, after the said hydrolysis, being covalently bonded to E.
Use of these silane compounds for functionalizing solid supports and for immobilizing biological molecules on these supports.

2 Claims, 2 Drawing Sheets

SILANE COMPOUNDS AND THEIR USE IN FUNCTIONALIZING SOLID SUPPORTS AND IMMOBILIZING BIOLOGICAL MOLECULES ON THESE SUPPORTS

This application is a National Stage application of International Application No. PCT/EP2007/050983 filed Feb. 1, 2007, the entire contents of which are hereby incorporated herein by reference. This application also claims the benefit under 35 U.S.C. §119 of French Patent Application No. 0650360, filed Feb. 1, 2006 the entire contents of which are hereby incorporated herein by reference.

TECHNICAL FIELD

The present invention relates to novel silane compounds which can be used in functionalizing solid supports, to supports functionalized by the said silane compounds and to their uses in immobilizing biological molecules, such as nucleic acids, poly-peptides, lipids, carbohydrates and hormones.

Supports carrying immobilized biological molecules are advantageously used for the detection and recognition of biological entities but also other applications, such as chemical synthesis or modification on a support.

As regards the detection and recognition of biological entities, it is essential to have available functionalized solid supports exhibiting the following characteristics:
  to make possible the reproducible immobilization of the biological molecules of interest;
  to make possible the immobilization of the biological molecules of interest in a sensitive fashion, the sensitivity of a functionalized solid support depending on the degree of immobilization and on the method of detection of a signal but also on the level of the background noise;
  to be reusable.

Biological molecules of interest are generally immobilized on solid supports in two stages:
  a first stage of functionalization of the supports, which consists of a chemical modification of their surface by grafting coupling agents which will provide for the attaching of the biological molecules to the support;
  a second stage of immobilization, which consists in establishing a covalent bond between the biological molecules and the coupling agents grafted to the support.

The coupling agents are grafted to the surface of the supports by reaction between —OH or hydride functional groups of the support and reactive functional groups of the agent, in order to form strong ionic or covalent interactions between the coupling agent and the support, and are arranged at the surface of the support generally in the form of a dense monolayer organized at the surface, for example, by formation of bonds of the Van der Waals type between the grafted molecules of coupling agents.

Coupling agents for functionalizing supports, in particular silicon-based supports, are organosilanes comprising at least one organic group R capable of reacting with a functional end of the molecules to be immobilized and at least one group X capable of reacting with the —OH or hydride functional groups of the support to form an ionic/covalent, indeed even covalent, bond.

Once the coupling agents are grafted and optionally arranged in the form of a monolayer at the surface of the support, the biological molecules can be grafted or adsorbed by reaction with an end functional group of the grafted coupling agent. A particularly attractive end functional group is the hydroxyl functional group, in particular primary hydroxyl functional group, for the following reasons:
  it makes possible the formation of a covalent bond by reacting with an appropriate group, for example a phosphoramidite group attached to the biological molecule to be immobilized;
  it makes possible the formation of noncovalent bonds of the "hydrogen bond" type on contact with an —NH$_2$, —OH or —SH functional group situated on the biological molecule to be immobilized.

The synthesis of silylated coupling agents carrying an alcohol functional group cannot be envisaged without involving protection of this functional group as a result of its very high reactivity, in particular with chlorosilane, alkoxysilane and hydrosilane groups, which protection is removed with grafting of the agent to the support.

Various techniques for obtaining silylated coupling agents carrying a hydroxyl functional group grafted to the surface of a support have been envisaged:
  the grafting to a silica support of a silylated agent carrying an ester functional group, followed by a reduction of the said ester functional group to give an alcohol, according to the following scheme:

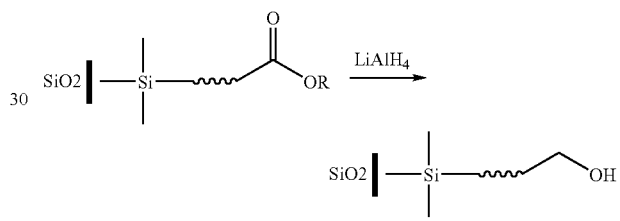

the grafting to a silica support of a silylated agent carrying a vinyl functional group, followed by an oxidation of the said vinyl functional group to give an alcohol, according to the following scheme:

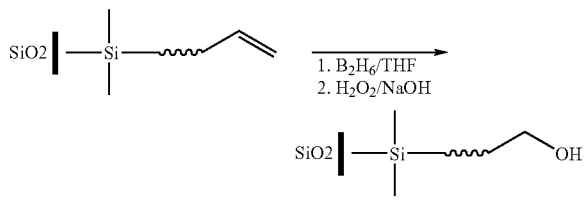

the grafting to a silica support of a silylated agent carrying a carbonate functional group, followed by a conversion of the carbonate functional group to give an alcohol by irradiation at a given wavelength, according to the following scheme:

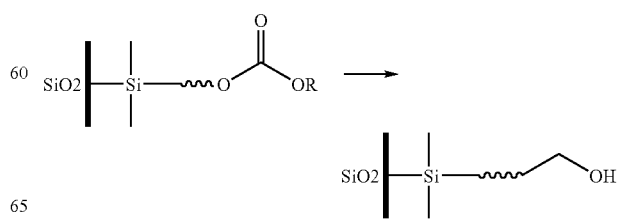

the grafting to a silica support of a silylated agent carrying a photolabile ether functional group, followed by a conversion of the ether functional group to give an alcohol by irradiation at a given wavelength, according to the following scheme:

$$SiO_2 \text{—}Si\text{—}\sim\sim O\text{—}CH_2\text{—}\langle\text{2-nitrophenyl}\rangle \longrightarrow SiO_2\text{—}Si\text{—}\sim\sim OH$$

All the operating conditions necessary for the release of the —OH functional group from the agents after grafting mentioned above are aggressive conditions which are harmful to the integrity of the support.

There thus exists a true need for coupling agents of the silane type which are capable of being grafted to the surface of an inorganic support and which are capable of releasing an —OH functional group after grafting under conditions which do not harm the nature of the support.

It is on the basis of this need that the inventors have developed novel silane compounds which exhibit the above-mentioned advantages.

ACCOUNT OF THE INVENTION

Thus, the invention relates, according to a first subject-matter, to a silane compound corresponding to the following formula (I):

A-E-X    (I)

in which:
X represents a silylated group capable of creating a covalent bond after reaction with the hydroxyl or hydride functional groups of a support;
E represents an organic spacer group;
A represents a group capable of forming an —OH functional group by acid hydrolysis, the said —OH functional group, after the said hydrolysis, being covalently bonded to E,
the said group A advantageously being an ether group chosen from methoxymethyl ether, t-butoxymethyl ether, 2-(trimethylsilyl)ethoxymethyl ether, tetrahydropyranyl ether, 1-methoxycyclohexyl ether, 4-methoxytetrahydropyranyl ether, 4-methoxy-tetrahydrothiopyranyl ether, 4-methoxytetrahydrothio-pyranyl S,S-dioxide ether, 1-[(2-chloro-4-methyl)-phenyl]-4-methoxypiperidin-4-yl ether, 1-[(2-fluoro-phenyl)phenyl]-4-methoxypiperidin-4-yl ether, 1,4-di-oxan-2-yl ether, tetrahydrofuranyl ether, 1-ethoxyethyl ether, 1-(2-chloroethoxy)ethyl ether, 1-methyl-1-methoxyethyl ether, 1-methyl-1-benzyloethyl ether, t-butyl ether, allyl ether, p-methoxybenzyl ether, p-halobenzyl ether, triphenylmethyl ether, triisopropylsilyl ether, dimethylisopropylsilyl ether, diethylisopropylsilyl ether or methoxymethyl carbonate groups.

The conversion which can be envisaged of the group A to give an —OH functional group by simple acid hydrolysis is particularly advantageous in the sense that acid hydrolysis does not interfere with the quality, the accessibility and the reproducibility of the surfaces of the supports on which the silane compounds of the invention are intended to be grafted.

According to the invention, the group A is a group capable of forming an —OH functional group by acid hydrolysis. In other words, the group A is a protective group for an —OH functional group, which group hydrolyses in an acid medium to release the said functional group.

Advantageously, this group is an ether group capable of releasing an —OH functional group by acid hydrolysis.

Such an ether group can advantageously be:

a methoxymethyl ether group of following formula:

$$CH_3\text{—}O\text{—}CH_2\text{—}O\text{—}$$

a t-butoxymethyl ether group of following formula:

$$H_3C\text{—}\underset{\underset{CH_3}{|}}{\overset{\overset{CH_3}{|}}{C}}\text{—}O\text{—}CH_2\text{—}O\text{—}$$

a 2-(trimethylsilyl)ethoxymethyl ether group of following formula:

$$H_3C\text{—}\underset{\underset{CH_3}{|}}{\overset{\overset{CH_3}{|}}{Si}}\text{—}CH_2\text{—}CH_2\text{—}O\text{—}CH_2\text{—}O\text{—}$$

a tetrahydropyranyl ether group of following formula:

$$\langle\text{tetrahydropyran}\rangle\text{—}O\text{—}$$

a 1-methoxycyclohexyl ether group of following formula:

$$\langle\text{cyclohexyl}\rangle(\text{—}O\text{—}CH_3)(\text{—}O\text{—})$$

a 4-methoxytetrahydropyranyl ether group of following formula:

$$\langle\text{tetrahydropyran}\rangle(\text{—}O\text{—}CH_3)(\text{—}O\text{—})$$

a 4-methoxytetrahydrothiopyranyl ether group of following formula:

a 4-methoxytetrahydrothiopyranyl S,S-di-oxide ether group of following formula:

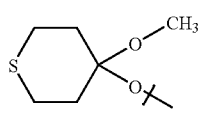

a 1-[(2-chloro-4-methyl)phenyl]-4-methoxypiperidin-4-yl ether group of following formula:

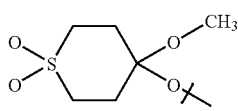

a 1-[(2-fluorophenyl)phenyl]-4-methoxy-piperidin-4-yl ether group of following formula:

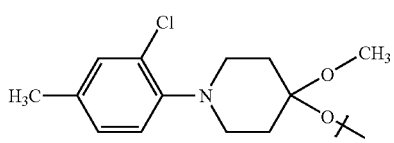

a 1,4-dioxan-2 yl ether group;
a tetrahydrofuranyl ether group;
a 1-ethoxyethyl ether group of following formula:

$CH_3—CH_2—O—CH_2—CH_2—O$⫤ a 1-(2-chloroethoxy)ethyl ether group of following formula:

$Cl—CH_2—CH_2—O—CH_2—CH_2—O$⫤ a 1-methyl-1-methoxyethyl ether group of following formula:

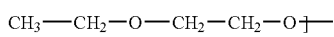

a 1-methyl-1-benzyloethyl ether group of following formula:

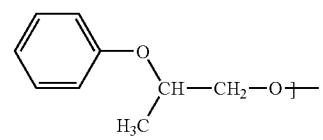

a t-butyl ether group of following formula:

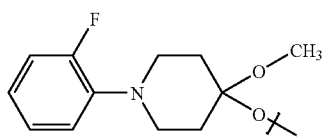 [SMILES: COC1(OC)CCN(c2ccccc2F)CC1]

an allyl ether group of following formula:

$H_2C=CH—CH_2—O$⫤ a p-methoxybenzyl ether group of following formula:

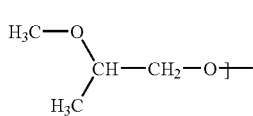

a p-halobenzyl ether group of following formula:

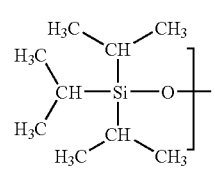

in which X represents a halogen atom;
a triphenylmethyl ether group of following formula:

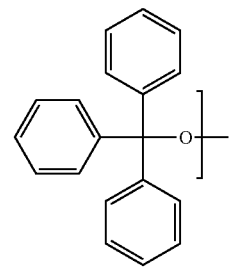 [SMILES: COC(c1ccccc1)(c1ccccc1)c1ccccc1]

a triisopropylsilyl ether group of following formula:

a dimethylisopropylsilyl ether group of following formula:

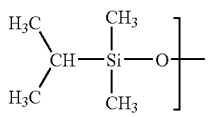

a diethylisopropylsilyl ether group;

a methoxymethyl carbonate group of following formula:

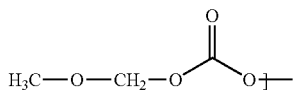

the cleavage lines indicating the point via which bonding takes place with the group E.

According to the invention, the group E is an organic spacer group, its essential role being to confer specific properties on the film resulting from the grafting of the silane compounds to the surface of a support.

This group E is generally a hydrocarbon group comprising, for example, from 2 to 24 carbon atoms and optionally comprising one or more unsaturations and/or one or more aromatic groups and/or one or more heteroatoms.

By way of examples, the group E can be an alkylene group, that is to say a sequence of —CH$_2$-type, comprising, for example, from 8 to 24 carbon atoms. This type of group confers on the silane compounds, once grafted to a support, an ability to interact with one another by creation of interchain interactions and thus contributes to organized multilayers being obtained.

The group E can be a fluoroalkylene group comprising from 3 to 24 carbon atoms. These groups contribute to conferring, on the film resulting from the grafting of the silane compounds comprising them, properties which allow them to be used in chromatography and in electrophoresis.

The group E can be a hydrocarbon group comprising one or more unsaturations, for example of the acetylenic type. An example of such a group can be an alkylene group as defined above interrupted by one or more acetylenic unsaturations. When the group E comprises at least two unsaturations, it can confer on the silane compounds, once grafted to a support, an ability to crosslink.

The group E can also be a hydrocarbon group comprising one or more aromatic groups.

Mention may be made, for example, of a group E comprising aromatic groups conjugated with unsaturated linear groups, such as a group resulting from the linking of a phenylene-vinylene or phenylene-acetylene unit. These groups contribute to conferring nonlinear optical properties on the film resulting from the grafting of the silane compounds comprising them.

Mention may be made, for example, of a group E comprising pyrrole or thiophene units. These groups contribute to conferring electronic conduction properties on the film resulting from the grafting of the silane compounds comprising them.

Mention may be made, for example, of a group E comprising one or more aromatic groups substituted by one or more heteroatomic groups, such as a group comprising a sequence of quinone units or of diazo units. These groups contribute to conferring photo/electroluminescence properties on the film resulting from the grafting of the silane compounds comprising them.

According to the invention, X represents a silylated group which makes possible the covalent attachment of the silane compound to the hydroxyl or hydride functional groups of a support, which support can, for example, be a solid support made of silicon, of ITO (indium tin oxide) or of titanium oxide.

This group X can, for example, be a trihalosilane group (such as a trifluorosilane group or a trichlorosilane group); a trihydrosilane SiH$_3$ group; a trialkoxysilane —Si(OR)$_3$ group with R representing a saturated, linear or branched, C$_1$ to C$_6$ alkyl group or a phenyl group (such as a trimethoxysilane group, a triethoxysilane group or a triisopropoxysilane group); a triamino-alkoxyamine —Si(NR$^1$R$^2$)$_3$ group with R$^1$ and R$^2$ independently representing a saturated, linear or branched, C$_1$ to C$_6$ alkyl group or a phenyl group; an organometallic group (such as an organomagnesium group or an organolithium group); or a hydrolysable group.

Specific compounds in accordance with the invention correspond to the following formulae (II), (III) and (IV):

 (II)

 (III)

 (IV)

The compounds of the invention can be prepared by conventional synthetic methods accessible to an expert in organic synthesis.

By way of example, the compounds (II), (III) and (IV) can be prepared according to the following reaction scheme:

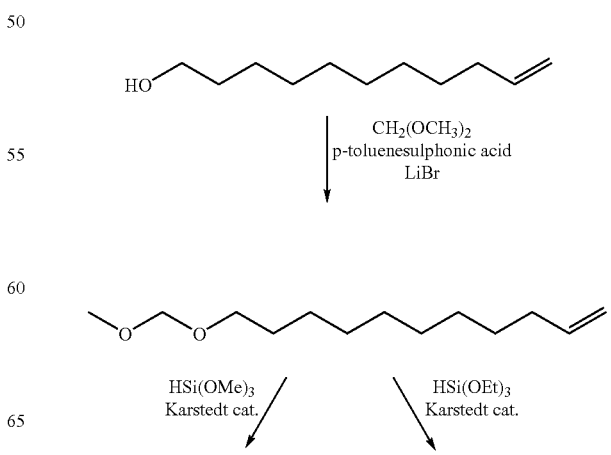

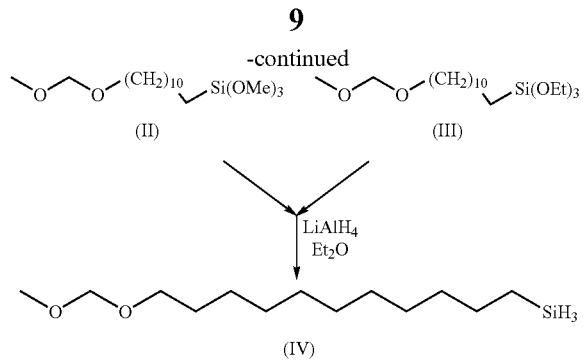

In this scenario, the methoxymethyl ether functional group is synthesized by reaction of undecenol with dimethoxymethane (acting both as reactant and as solvent) in the presence of catalytic amounts of lithium bromide and of para-toluenesulphonic acid. Finally, a silylated group is introduced via a hydrosilylation reaction in the presence of a Karstedt catalyst of formula $Pt[Si(CH_3)_2HC=CH_2]_2O$.

A person skilled in the art will adapt this reaction scheme according to the silane compounds which he wishes to obtain.

As mentioned above, the silane compounds of the invention are capable of being grafted to the surface of a support because of the presence of the group X capable of reacting with hydroxyl or hydride functional groups (present on the support) to form covalent bonds.

Thus, the invention relates, according to a second subject-matter, to a process for the functionalization of a solid support comprising hydroxyl or hydride functional groups at the surface, comprising a stage in which a solution comprising at least one silane compound is brought into contact with the said support, the said silane compound corresponding to the following formula (I):

in which:
X represents a silylated group capable of creating a covalent bond after reaction with the hydroxyl or hydride functional groups of a support;
E represents an organic spacer group;
A represents a group capable of forming an —OH functional group by acid hydrolysis, the said —OH functional group, after the said hydrolysis, being covalently bonded to E,
the said group A advantageously being an ether group chosen from methoxymethyl ether, t-butoxy-methyl ether, 2-(trimethylsilyl)ethoxymethyl ether, tetrahydropyranyl ether, 1-methoxycyclohexyl ether, 4-methoxytetrahydropyranyl ether, 4-methoxytetrahydrothiopyranyl ether, 4-methoxytetrahydrothiopyranyl S,S-dioxide ether, 1-[(2-chloro-4-methyl)phenyl]-4-methoxypiperidin-4-yl ether, 1-[(2-fluorophenyl)-phenyl]-4-methoxypiperidin-4-yl ether, 1,4-dioxan-2-yl ether, tetrahydrofuranyl ether, 1-ethoxyethyl ether, 1-(2-chloroethoxy)ethyl ether, 1-methyl-1-methoxyethyl ether, 1-methyl-1-benzyloethyl ether, t-butyl ether, allyl ether, p-methoxybenzyl ether, p-halobenzyl ether, triphenylmethyl ether, triisopropylsilyl ether, dimethylisopropylsilyl ether, diethylisopropylsilyl ether or methoxymethyl carbonate groups.

X and E can be defined exactly as in the part in which the silane compounds are described.

In particular, X can, for example, be a trihalosilane group (such as a trifluorosilane group or a trichlorosilane group); a trihydrosilane $SiH_3$ group; a trialkoxysilane $—Si(OR)_3$ group with R representing a saturated, linear or branched, $C_1$ to $C_6$ alkyl group or a phenyl group (such as a trimethoxysilane group, a triethoxysilane group or a triisopropoxysilane group); a triaminoalkoxyamine $—Si(NR^1R^2)_3$ group with $R^1$ and $R^2$ independently representing a saturated, linear or branched, $C_1$ to $C_6$ alkyl group or a phenyl group; an organometallic group (such as an organomagnesium group or an organolithium group); or a hydrolysable group.

Compounds of formulae (II) to (IV) are particularly appropriate for the implementation of this process.

This process can comprise, beforehand, a stage of treatment of the support surface in order to create, on the said surface, the hydroxyl or hydride functional groups necessary for the grafting.

Thus, for a silicon support of the 100 type (for example of the wafer type), it is preferable, before functionalization, to treat the latter by bringing it into contact with a sodium hydroxide solution in order to bring about a hydroxylation reaction.

The supports which can be functionalized according to the process of the invention can be organic supports (for example made of plastics), inorganic supports, for example supports made of metal oxide (for example silica and its derivatives, such as glass, quartz, indium tin oxide, and the like), metal supports (such as supports made of titanium) or supports made of silicon, the essential point being that these supports are capable (optionally with the preliminary treatment stage mentioned above) of exhibiting hydroxyl or hydride functional groups for the grafting of the silane compounds of the invention.

Another subject-matter of the invention is the functionalized solid support capable of being obtained by the process of the invention.

Another subject-matter of the present invention is thus a process for the immobilization of biological molecules on a functionalized solid support, comprising the following stages:

a) a stage of functionalization of a solid support comprising hydroxyl or hydride functional groups at the surface, comprising a stage in which the said support is brought into contact with a solution comprising at least one silane compound corresponding to the following formula (I):

in which:
X represents a silylated group capable of creating a covalent bond after reaction with the hydroxyl or hydride functional groups of a support;
E represents an organic spacer group;
A represents a group capable of forming an —OH functional group by acid hydrolysis, the said —OH functional group, after the said hydrolysis, being covalently bonded to E, b) a stage of deprotection by acid hydrolysis of the —OH functional groups of the grafted silane compounds;

c) a stage in which the support obtained in stage b) is brought into contact with a solution comprising the biological molecule(s) to be immobilized, the said biological molecules comprising an end capable of reacting with the —OH functional groups of the grafted silane compounds to form a covalent bond.

According to one alternative, the biological molecule(s) to be immobilized can be grafted not directly to the deprotected —OH functional group of the silane compound but to a different functional group introduced by reaction of a compound comprising it with the deprotected —OH functional group of the silane compound.

In this case, the process of the invention comprises the following stages:

a) the preparation of a functionalized solid support by carrying out a stage of functionalization of a solid support comprising hydroxyl or hydride functional groups at the surface, which consists in bringing into contact with the said support a solution comprising at least one silane compound corresponding to the following formula (I):

$$A-E-X \qquad (I)$$

in which:
- X represents a silylated group capable of creating a covalent bond after reaction with the hydroxyl or hydride functional groups of a support;
- E represents an organic spacer group;
- A represents a group capable of forming an —OH functional group by acid hydrolysis, the said —OH functional group, after the said hydrolysis, being covalently bonded to E, b) a stage of deprotection by acid hydrolysis of the —OH functional groups of the grafted silane compounds;

c1) a stage in which the support obtained in b) is brought into contact with a compound which is capable of forming a covalent bond by reaction with the —OH functional group of the silane compounds and which comprises, on conclusion of this stage, a reactive end other than an —OH functional group;

c2) a stage in which the support obtained in stage c1) is brought into contact with a solution comprising the biological molecule(s) to be immobilized, the said biological molecules comprising an end capable of reacting with the said reactive end to form a covalent bond.

A, X and E can be defined exactly as in the part in which the silane compounds are described.

In particular, X can, for example, be a trihalosilane group (such as a trifluorosilane group or a trichlorosilane group); a trihydrosilane $SiH_3$ group; a trialkoxysilane —$Si(OR)_3$ group with R representing a saturated, linear or branched, $C_1$ to $C_6$ alkyl group or a phenyl group (such as a trimethoxysilane group, a triethoxysilane group or a triisopropoxysilane group); a triaminoalkoxyamine —$Si(NR^1R^2)_3$ group with $R^1$ and $R^2$ independently representing a saturated, linear or branched, $C_1$ to $C_6$ alkyl group or a phenyl group; an organometallic group (such as an organomagnesium group or an organolithium group); or a hydrolysable group.

In particular, A is advantageously an ether group chosen from methoxymethyl ether, t-butoxymethyl ether, 2-(trimethylsilyl)ethoxymethyl ether, tetrahydropyranyl ether, 1-methoxycyclohexyl ether, 4-methoxytetrahydropyranyl ether, 4-methoxytetrahydro-thiopyranyl ether, 4-methoxytetrahydrothiopyranyl S,S-dioxide ether, 1-[(2-chloro-4-methyl)phenyl]-4-methoxypiperidin-4-yl ether, 1-[(2-fluorophenyl)-phenyl]-4-methoxypiperidin-4-yl ether, 1,4-dioxan-2-yl ether, tetrahydrofuranyl ether, 1-ethoxyethyl ether, 1-(2-chloroethoxy)ethyl ether, 1-methyl-1-methoxyethyl ether, 1-methyl-1-benzyloethyl ether, t-butyl ether, allyl ether, p-methoxybenzyl ether, p-halobenzyl ether, triphenylmethyl ether, triisopropylsilyl ether, dimethylisopropylsilyl ether, diethylisopropylsilyl ether or methoxymethyl carbonate groups.

Compounds of formulae (II) to (IV) are particularly appropriate for the implementation of this process.

The deprotection stage can be carried out by subjecting the grafted support to an acid solution, for example an aqueous hydrochloric acid solution.

These functionalized supports, once the —OH functional groups have been deprotected, make possible the reproducible immobilization of biological molecules of interest while limiting the nonspecific adsorption of molecules.

These functionalized supports can in particular be used for the immobilization, by covalent attachment, of biological molecules of interest, such as nucleic acids, polypeptides (proteins, enzymes), lipids, carbohydrates or hormones.

Within the meaning of the present invention and in what follows, the term "nucleic acids" is under-stood to mean both oligonucleotides and DNAs or RNAs, or also nucleic acids with the backbone or bases modified, such as peptide nucleic acids (PNA), which involve peptide bonds in place of phosphodiester bonds.

Thus, in order to graft a nucleic acid to the support, it may be possible to envisage grafting, to the —OH functional groups of the silane compounds, a compound comprising a phosphate group, which group will be capable of reacting with a nucleotide to form a phosphodiester bond, the subsequent nucleotides reacting, the one with the other, to form the polynucleotide.

An appropriate compound comprising a phosphate group is Cy3-phosphoramidite, which also acts as fluorescent marker.

Once deprotected, the grafted silane compounds exhibit a hydrophilic nature. They can also be used to provide a function of retention of hydrophilic compounds, such as proteins.

Another subject-matter of the invention is the solid supports obtained by employing the immobilization process in accordance with the invention, that is to say the solid supports on which the biological molecules of interest are immobilized by covalent attachment.

These solid supports can thus be used as analytical tools (for example for diagnosis or sequencing) or as synthetic tools for producing, for example, coatings.

The supports thus have applications in numerous fields, such as synthesis on solid supports, the separation and purification of molecules (electrophoresis and chromatography), or biosensors.

The use of functionalized solid supports according to the present invention makes it possible to immobilize different types of biological molecules and thus to prepare different types of chips, such as nucleic acid chips, for example DNA chips, or poly-peptide chips, for example protein chips.

The use of modified solid supports according to the present invention is particularly advantageous in the preparation of DNA chips, namely supports to which oligo- or polynucleotides with known sequences are covalently attached. Such DNA chips make it possible, by hybridization of the oligo- or polynucleotides immobilized on the support with target nucleic acids or oligonucleotides, to determine the sequence of these target molecules and to monitor the expression of the genes.

Another subject-matter of the present invention is thus a nucleic acid or polypeptide chip obtained by the immobilization process of the invention mentioned above.

The invention will now be described with respect to the examples given below by way of illustration and without implied limitation.

DETAILED ACCOUNT OF SPECIFIC EMBODIMENTS

Example 1

Figure 1:
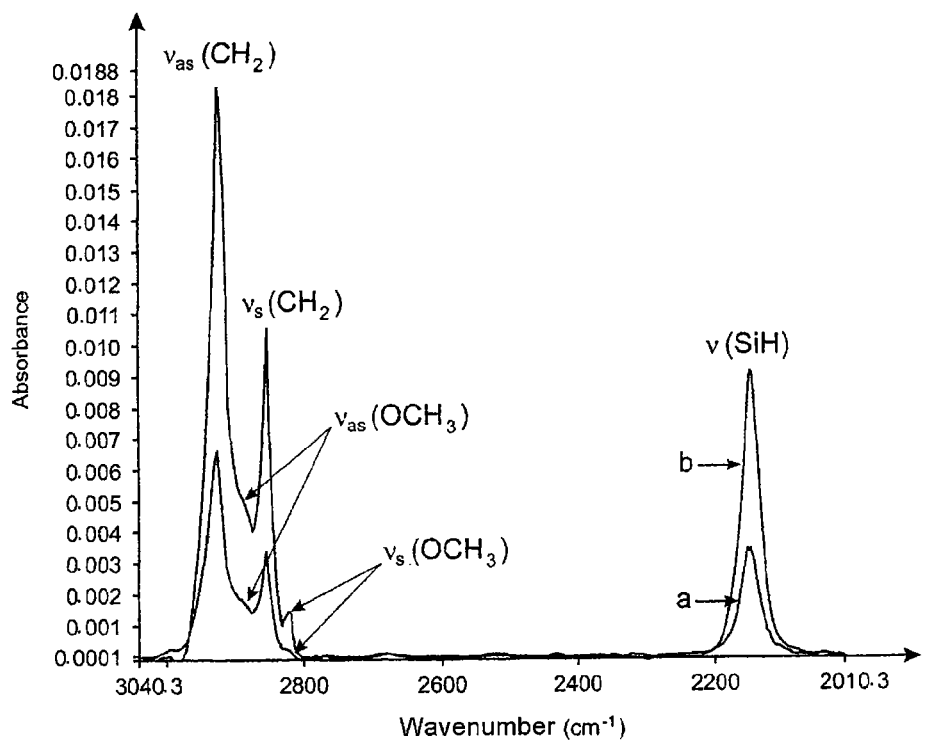
FIG. 1 illustrates the IR spectrum of 11-(methoxymethoxy)undecylsilane in solution (curve a) in tricholorethylene and after grafting (curve b).

This example illustrates the synthesis of a silane in accordance with the invention: 11-(methoxy-methoxy)undecylsilane according to the following reaction scheme:

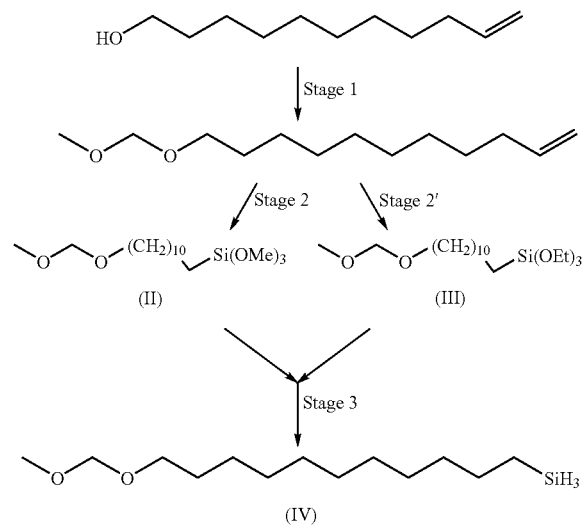

The methoxymethyl ether functional group is synthesized by reaction of undecenol with dimethoxy-methane (reactant and solvent) in the presence of catalytic amounts of lithium bromide and of para-toluenesulphonic acid. The incorporation of the silylated group takes place via a hydrosilylation reaction in the presence of a Karstedt catalyst.

a) Stage 1: Synthesis of 11-(methoxymethoxy)undec-1-ene

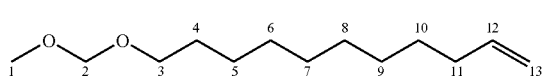

Lithium bromide (3.06 g, 35 mmol, 0.4 eq) and para-toluenesulphonic acid (1.67 g, 8.8 mmol, 0.1 eq) are added to a solution of undecenol (15 g, 17.65 ml, 88 mmol) dissolved in 225 ml of dimethoxymethane (12.9 g, 170 mmol, 28.3 eq). The reaction takes place at ambient temperature for 12 hours. After addition of 500 ml of ether, the reaction mixture is washed successively with deionized water (twice) and with a saturated sodium chloride solution, dried over anhydrous magnesium sulphate and then concentrated. The residue is purified by chromatography on a column of silica gel (pentane/ether: 97.5/12.5) to give a yellowish liquid.

The characteristics of the product obtained are as follows:
Weight: 16.26 g
Yield: 86%
$^1$H NMR (200 MHz, CDCl$_3$): 1.31 (12H, m, H$^{5-10}$), 1.57 (2H, m, H$^4$), 2.03 (2H, m, H$^{11}$), 3.37 (3H, s, H$^1$), 3.52 (2H, t, H$^3$, $^3J_{H-H}$=6.6 Hz), 4.62 (2H, s, H$^2$), 4.96 (2H, m, H$^{13}$) 5.82 (1H, m, H$^{12}$)
$^{13}$C NMR (200 MHz, CDCl$_3$): 26.59, 29.30, 29.49, 29.80 (2C), 29.91, 30.12, 34.18 (C$^{11}$), 55.37 (C$^1$), 68.20 (C$^3$), 96.74 (C$^2$), 114.47 (C$^{13}$), 139.50 (C$^{12}$)
Mass spectrometry m/z (NBA): 154 [M+H]$^+$—O—CH$_2$OCH$_3$ b) Stage 2: Synthesis of 11-(methoxymethoxy)undecyl-trimethoxysilane (II)

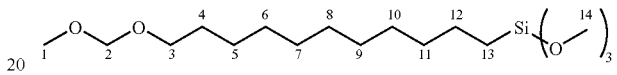

11-(Methoxymethoxy)undec-1-ene (12.6 g, 59 mmol) is mixed with trimethoxysilane (95 w) (9.65 g, 10.1 ml, 75 mmol, 1.3 eq). The Karstedt catalyst (0.14 g, 0.15 mmol, 0.0025 eq) is added very slowly. The reaction takes place at ambient temperature for 16 hours. The crude reaction product is purified by distillation to give a colourless liquid (B.p.: 125-130° C. at a pressure of 0.5 mbar).

The characteristics of the product obtained are as follows:
Weight: 14.08 g
Yield: 71%
$^1$H NMR (200 MHz, CDCl$_3$): 0.65 (2H, m, H$^{13}$), 1.29 (16H, m, H$^{5-12}$), 1.59 (2H, m, H$^{4^2}$), 3.62 (3H, s, H$^1$), 3.52 (2H, t, H$^3$, $^3J_{H-H}$=6.5 Hz), 3.58 (9H, s, H$^{14}$), 4.62 (2H, s, H$^2$)
$^{13}$C NMR (200 MHz, CDCl$_3$): 9.44 (C$^{13}$), 22.92, 26.55, 29.59, 29.78, 29.83, 29.92 (2C), 30.07, 33.46, 50.75 (3C, C$^{14}$), 55.33 (C$^1$), 68.18 (C$^3$), 96.68 (C$^2$)
Si NMR (200 MHz, CDCl$_3$): −41.31 (S)

Stage 2': Synthesis of 11-(methoxymethoxy)undecyl-triethoxysilane (III)

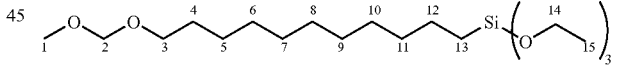

11-(Methoxymethoxy)undec-1-ene (15.66 g, 73 mmol) is mixed with triethoxysilane (97%) (19.94 g, 22.4 ml, 118 mmol, 1.61 eq). The Karstedt catalyst (0.18 g, 0.19 mmol, 0.0025 eq) is added very slowly. The reaction takes place at ambient temperature for 3 hours. The crude reaction product is purified by distillation to give a colourless liquid (B.p.: 105-110° C. at a pressure of 10$^{-2}$ mbar).

The characteristics of the product obtained are as follows:
Weight: 19.61 g
Yield: 71%
$^1$H NMR (200 MHz, CDCl$_3$): 0.64 (2H, m, H$^{13}$), 1.24 (9H, t, H$^{15}$, $J_{H-H}$=7.0 Hz), 1.27 (16H, m, H$^{5-12}$), 1.60 (2H, m, H$^4$), 3.37 (3H, s, H$^1$), 3.53 (2H, t, H$^3$, $^3J_{H-H}$=6.6 Hz), 3.82 (6H, q, H$^{14}$, $^3J_{H-H}$=7.0 Hz), 4.63 (2H, s, H$^2$)
$^{13}$C NMR (200 MHz, CDCl$_3$): 10.78 (C$^{13}$), 18.67 (3C, $^{15}$C), 23.14, 26.60, 29.63, 29.83, 29.90, 29.98 (2C), 30.14, 33.57, 55.42 (C$^1$), 58.65 (3C, C$^{14}$), 68.26 (C$^3$), 96.77 (C$^2$)
Si NMR (200 MHz, CDCl$_3$): −44.27 (s)
Mass spectrometry m/z (NBA): 379 [M+H]$^+$

Stage 3: Synthesis of 11-(methoxymethoxy)undecylsilane (IV)

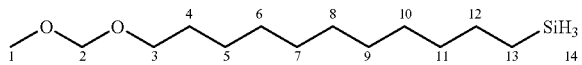

A solution of 11-(methoxymethoxy)undecyl-triethoxysilane (17.34 g, 49 mmol) dissolved in 500 ml of anhydrous ether is slowly added to a solution of $LiAlH_4$ (3.5 g, 92 mmol, 2 eq) in 500 ml of anhydrous ether cooled to 0° C. The reaction takes place at ambient temperature and under argon for 48 hours. The reaction mixture is filtered through celite and then concentrated, and the residue is taken up in dichloromethane. Subsequently, the organic phase is washed successively with a 1N hydrochloric acid solution (twice) and with a saturated sodium chloride solution, dried over anhydrous magnesium sulphate and then concentrated. The residue is purified by distillation to give a colourless liquid (B.p.: 75-80° C. at a pressure of $10^{-2}$ mbar).

The characteristics of the product obtained are as follows:
Weight: 8.46 g
Yield: 75%
$^1$H NMR (200 MHz, $CDCl_3$): 0.75 (2H, m, $H^{13}$), 1.24 (16H, m, $H^{5-12}$), 1.61 (2H, m, $H^4$), 3.37 (3H, s, $H^1$), 3.50 (3H, t, $H^{14}$, $^3J_{H-H}$=3.9 Hz), 3.54 (2H, t, $H^3$, $^3J_{H-H}$=6.5 Hz), 4.64 (2H, s, $H^2$)
$^{13}$C NMR (200 MHz, $CDCl_3$): 6.30 ($C^{13}$), 26.72, 26.75, 29.64, 29.84, 29.88, 29.98 (2C), 30.15, 32.88, 55.40 ($^1C$), 68.23 ($C^3$), 96.76 ($C^2$)
Si NMR (200 MHz, $CDCl_3$): −58.96 (s)
Mass spectrometry m/z (NBA): 245 $[M+H]^+$

Example 2

This example illustrates the silanization of a silicon support with the silane compound prepared in Example 1.

Beforehand, the silicon support, covered with a thermal oxide layer with a thickness of 5000 Å, is subjected to hydroxylation by bringing it into contact with a 3.5M sodium hydroxide solution for two hours.

A solution comprising the silane compound of Example 1 at a concentration of $10^{-2}$M in anhydrous trichloroethylene is used and the silanization reactions are carried out at a controlled temperature of 2° C. for 24 hours. The methoxymethoxy functional group is converted to an OH functional group during a post-silanization reaction of the modified support by bringing it into contact with a 12N hydrochloric acid solution, such as that illustrated in FIG. 1.

FIG. 1 represents the infrared spectrum of 11-(methoxymethoxy)undecylsilane in solution in trichloroethylene and the spectrum of the surface of the silicon support after silanization.

Other experimental results appear in the table below.

|  | Compound of Example 1 in solution in trichloroethylene | Compound of Example 1 grafted at the surface of the support |
|---|---|---|
| Contact angle | — | 75° ± 2 |
| Roughness (nm) | — | 0.18 |
| Ellipsometry (nm, n = 1.45) | — | 2.2 ± 0.1 |

|  | Compound of Example 1 in solution in trichloroethylene | Compound of Example 1 grafted at the surface of the support |
|---|---|---|
| ATR |  |  |
| $\nu_{as}(CH_2)$, $cm^{-1}$ | 2928 | 2926 |
| $\nu_s(CH_2)$, $cm^{-1}$ | 2855 | 2854 |
| $\nu_{as}(CH_3)CH_2$—O—$CH_3$, $cm^{-1}$ | 2885 | 2885 |
| $\nu_s(CH_3)CH_2$—O—$CH_3$, $cm^{-1}$ | 2822 | 2823 |
| $\nu(SiH)$, $cm^{-1}$ | 2149 | 2150 |

After silanization, the bands characteristic of the singly attached hydrosilane of Example 1 are observed by IR-ATR spectroscopy. The surface of the support thus modified is relatively hydrophobic (contact angle of 75°) and the monolayer obtained, with a thickness of 2.2 nm, is homogeneous (roughness of 0.18 nm).

Example 3

This example illustrates the deprotection of the —OH functional group of the grafted compound at the surface of the support, this deprotection reaction being monitored either by the study of the change in the contact angle or by Fourier transform IR-ATR (FTIR-ATR) spectroscopy.

a) Study of the Change in the Contact Angle

Monitoring by contact angle was carried out in order to demonstrate the speed and effectiveness of the deprotection treatment.

For this, the silicon support functionalized with the silane compound carrying a methoxymethoxy group at the chain end is immersed in a 12N HCl solution. After rinsing with deionized water and with pentane under ultrasound for four minutes, the contact angle is measured.

Figure 2:
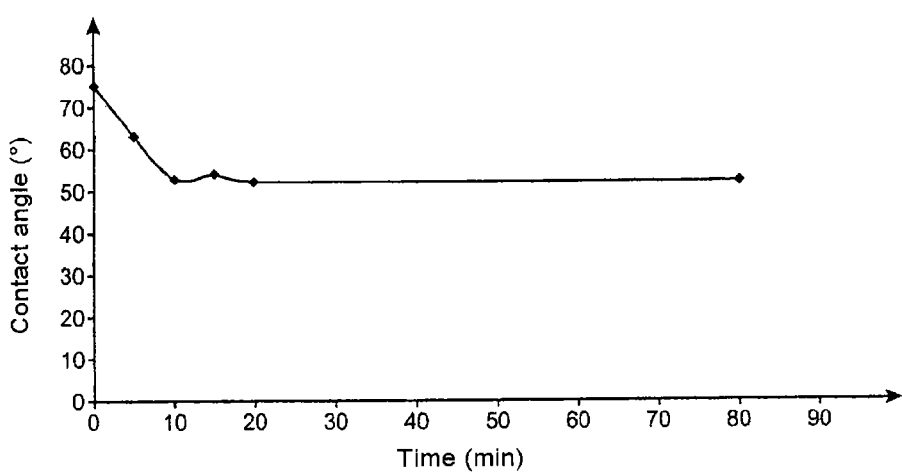
FIG. 2 is a graph illustrating the change in the contact angle of a grafted silicon support as a function of the immersion time in a 12N hydrochloric acid solution during the deprotection of the methoxy-methoxy functional group.

FIG. 2 illustrates the change in the contact angle as a function of the contact time of the support with the HCl solution.

The following results are presented in the table below.

| Contact time (min) | Contact angle (°) |
|---|---|
| 0 | 75.1 |
| 5 | 63 |
| 10 | 52.9 |
| 15 | 54.1 |
| 20 | 52.2 |
| 80 | 52.1 |

These results show that the reaction of the hydrochloric acid solution with the surface results in a fall in the contact angle from approximately 75° to approximately 52°, which confirms the replacement of the methoxymethoxy functional group by a much more hydrophilic —OH functional group. Furthermore, it was found that the deprotection reaction is fast. After reacting for 5 minutes, the value has already fallen by 10° and, after reacting for 10 minutes, the surface is completely deprotected. It is also important to point out that the angle does not substantially vary any more, even after immersion for a long time in this aggressive solution, which attests to the stability of the monolayer deposited.

b) Monitoring of the Deprotection Reaction by FTIR-ATR

In order to confirm the results obtained in the preceding section, the deprotection reaction was monitored by FTIR-ATR.

Figure 3:
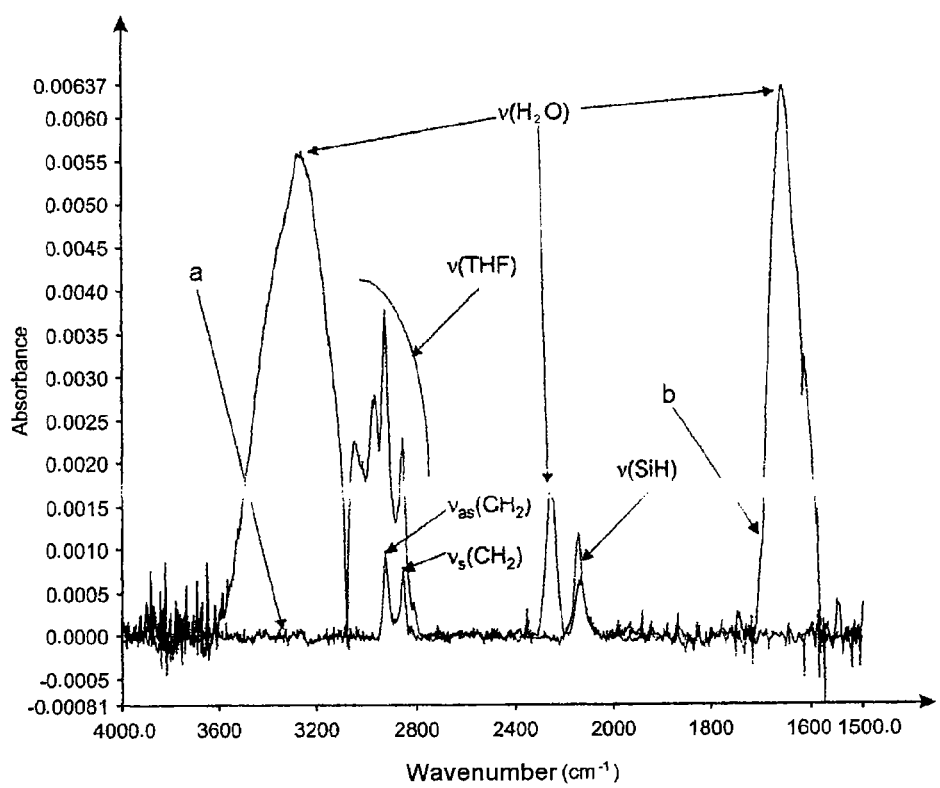
FIG. 3 illustrates the IR spectrum of the surface of a silicon support grafted with a silane compound of the invention before deprotection and after deprotection.

FIG. 3 illustrates the FTIR-ATR spectrum of:
- the surface of the support grafted with the nondeprotected silane compound after successive washing operations with water, THF and trichloroethylene (curve a);
- the surface of the support grafted with the deprotected silane compound after treatment with the 12N HCl solution for 15 minutes and successive washing operations with water, THF and trichloroethylene (curve b).

In curve a, it may be observed that no trace remains of the bands characteristic of water and of THF (hydrophilic compounds). This observation is entirely in agreement with the presence at the surface of the hydrophobic methoxymethoxy functional group, which does not promote the physical adsorption of these protic solvents. The minor appearance of the $\upsilon_a$ (CH$_2$), $\upsilon_{as}$ (CH$_2$) and $\upsilon_{as}$ (SiH) bands can be explained by a slight reorganization of the chains at the surface.

In contrast, once the treatment with the 12N HCl solution has been carried out, it is possible to observe, in curve b, the appearance of bands characteristic of water and THF, which attests to a physical adsorption of these solvents at the surface of the support. The change in behaviour of these protic solvents with regard to the surface of the support after treatment shows us that the deprotection of the methoxymethoxy functional groups (hydrophobic functional groups) to give —OH functional groups (hydrophilic functional groups) had indeed taken place.

c) Other Analyses

Other measurements were carried out (contact angle, roughness, thickness) and appear in the table below.

|  | Compound of Example 1 grafted to the support | Compound of Example 1 grafted at the surface and deprotected |
|---|---|---|
| Contact angle | 75° ± 2 | 52° ± 2 |
| Roughness (nm) | 0.18 | 0.2 |
| Ellipsometry (nm, n = 1.45) | 2.2 ± 0.1 | 1.8 ± 0.1 |
| ATR* | | |
| $\nu_{as}$(CH$_2$), cm$^{-1}$ | 2926 | 2926 |
| $\nu_s$(CH$_2$), cm$^{-1}$ | 2854 | 2854 |
| $\nu_{as}$(CH$_3$)CH$_2$—O—CH$_3$, cm$^{-1}$ | 2885 | — |
| $\nu_s$(CH$_3$)CH$_2$—O—CH$_3$, cm$^{-1}$ | 2823 | — |
| $\nu$(SiH), cm$^{-1}$ | 2150 | 2150 |

The analyses given above indicate that very low surface roughnesses are obtained after the deprotection reaction.

Finally, from the analyses carried out by ellipsometry, taking the refractive index of 1.45, a slight decrease in the thickness of the surface organic film from 2.2 to 1.8 nm after the deprotection stage is observed, which is explained by the conversion of the methoxymethoxy group to an —OH group.

Example 4

This example illustrates a coupling reaction of a fluorophore compound with the deprotected silane compound grafted to the silicon support prepared in accordance with Example 3.

The fluorophore compound is Cy3-phosphoramidite and corresponds to the following formula:

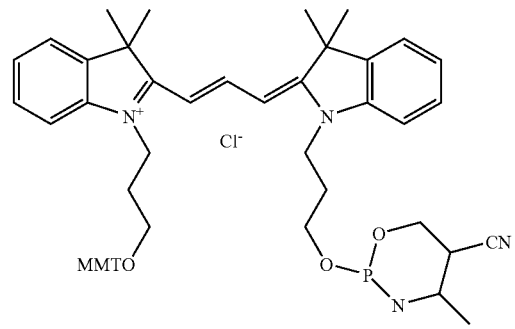

The coupling reaction is carried out in acetonitrile, with tetrazole, at ambient temperature for 10 minutes. This coupling reaction is followed by a capping stage in the presence of acetic anhydride and N-methylimidazole in order to mask the unreacted —OH groups. The phosphite compound obtained by reaction with Cy3-phosphoramidite is subsequently oxidized, to convert the phosphite group to a phosphate group, and, finally, a detritylation stage is carried out in order to allow the fluorophore compound to be visible with the GenePix® scanner from Axon.

It is apparent, on the image taken by the scanner, that the fluorophore compound has indeed been grafted to the support via —OH groups carried by the grafted silane compounds.

Example 5

This example illustrates the synthesis of an oligonucleotide comprising 20 bases from a support grafted with silane compounds in accordance with the invention.

The oligonucleotide is manufactured on an Expedite® synthesizer from Perkin-Elmer using 20 synthesis cycles and on the support produced in Example 4. At the end of the cycles, the exocyclic bases of the nucleotides are deprotected by an ammoniacal treatment (40% NH$_4$OH solution) at 55° C. for 30 minutes, which also makes possible the hydrolysis of the cyanoethoxyphosphate functional group originating from the Cy3-phosphoramidite fluorophore. Subsequently, the support is brought into contact with a solution comprising an oligonucleotide complementary to that synthesized in accordance with the procedure described above and comprising the Cy3-phosphoramidite fluorophore in a proportion of 0.2 µM in a saline sodium citrate buffer for 1 hour at 40° C.

The fluorescence measurement results show that the modified supports in accordance with the invention make possible the in situ synthesis of an oligonucleotide.

Example 6

This example illustrates the properties of retention of proteins by a modified support in accordance with the invention (support of Example 3).

A biological tissue, for example of cancerous nature, is affixed to the modified support for 30 seconds and then, after rinsing and depositing the matrix, analysis by mass spectrometry (obtained by a Seldi-T of device sold under the name ProteinChip® System Series 4000 by Ciphergen) is carried out directly on the surface.

The spectrum obtained shows the presence of peaks which can be assigned to proteins exhibiting hydrophilic affinities.
The invention claimed is:
1. A compound of following formula (II):
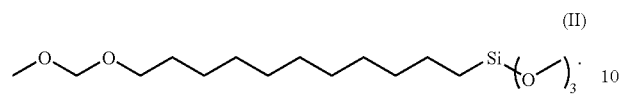
2. A compound of following formula (III):
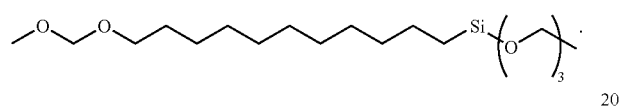
* * * * *